(12) United States Patent
Matsutani et al.

(10) Patent No.: US 6,908,471 B2
(45) Date of Patent: Jun. 21, 2005

(54) OPHTHALMOLOGIC KNIFE (75) Inventors: Kanji Matsutani, Tochigi-ken (JP);
Takashi Ina, Tochigi-ken (JP);
Masahiko Saito, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 09/939,579

(22) Filed: Aug. 28, 2001

(65) Prior Publication Data

US 2002/0026205 A1 Feb. 28, 2002

(30) Foreign Application Priority Data

Aug. 30, 2000 (JP) ........................................ 2000-260242

(51) Int. Cl.⁷ ............................................. A61B 17/32
(52) U.S. Cl. ....................................................... 606/167
(58) Field of Search ................................ 606/166, 167, 606/170, 107

(56) References Cited

U.S. PATENT DOCUMENTS

| | | | | | |
|---|---|---|---|---|---|
| 4,185,634 A | * | 1/1980 | Freedman | ..................... | 30/353 |
| 5,201,747 A | * | 4/1993 | Mastel | ......................... | 30/353 |
| 5,258,002 A | * | 11/1993 | Jeffers et al. | ............... | 606/167 |
| 5,352,233 A | * | 10/1994 | Anis | .......................... | 473/590 |
| 5,713,915 A | * | 2/1998 | Van Heugten et al. | ....... | 606/166 |
| 6,139,559 A | * | 10/2000 | Nordan et al. | .............. | 606/166 |
| 2001/0029386 A1 | * | 10/2001 | Matsutani et al. | .......... | 606/166 |

* cited by examiner

Primary Examiner—Glenn K. Dawson
Assistant Examiner—D. Jacob Davis
(74) Attorney, Agent, or Firm—Townsend & Banta (57) ABSTRACT

The present invention relates to an ophthalmologic knife for being guided into an incision formed at an eyeball and for widening the width of the incision, the ophthalmologic knife comprising a handle and a blade portion having a flat shape formed at a end portion of the handle. The blade portion is formed with cutting edges arranged on both sides in a narrowing manner toward a front tip of the blade portion, and the front tip of the blade portion is formed with a guide portion arranged between the two cutting edges for guiding the blade portion into the incision formed at the eyeball.

7 Claims, 10 Drawing Sheets

OPHTHALMOLOGIC KNIFE

BACKGROUND OF THE INVENTION

1. Field of the Invention

This invention relates to an ophthalmologic knife for widening a highly self-sealing incision formed at an eyeball to a width required for inserting an intraocular lens.

2. Description of Related Art

When performing ophthalmologic surgery for a cataract, a primary incision is formed at the cornea or between the cornea and the sclera, and a vacuum nozzle of a phacoemulsification device is inserted into the primary incision to extract the cloudy portion of a crystalline lens. In such case, the primary incision is formed with a width within the limit for inserting the vacuum nozzle so as to prevent intraocular fluid leakage. After a particular portion of the crystalline Tens is extracted, an intraocular lens is inserted; in such case, typically, the necessary width of the incision for such insertion is larger than the width of the primary incision, and a secondary incising for widening the primary incision is performed.

When incising is performed upon the cornea or between the cornea and the sclera in an ophthalmologic operation, a suture or a ligature of the incised cornea and the sclera is required. However, with such suture process, the sutural thread would pressure the cornea and the sclera to result to possibilities such as delay in vision recovery or causing of astigmatism; therefore, recently, instead of such suture, surgery is performed generally by forming an incision of a self-sealing nature, in which the incision could seal by itself.

Figure 7:
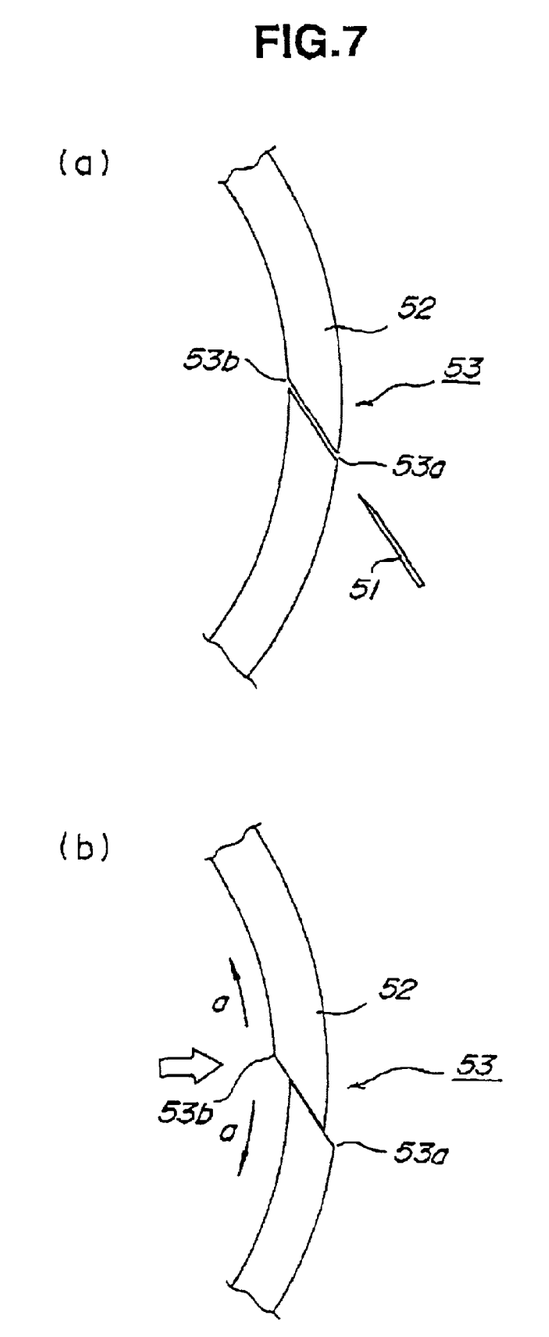
FIG. 7 is an explanatory view showing an incision of a highly self-sealing nature.

An incision of high self-sealing nature formed during the vacuuming of the crystalline lens will be explained with reference to FIG. 7. As shown in FIG. 7(*a*), when a cornea 52 is incised diagonally in a thickness direction with a knife 51 (Normally, looking from the front of the eyeball, the incising is performed by inserting the knife 51 diagonally upward from below), as shown in FIG. 7(*b*), an inner pressure of the eyeball works upon the cornea 52 in a widening direction (the direction where the cornea 52 is emerged as indicated with an arrow a) so that the incised portion of the cornea 52 would be pressed together and sealed for forming an incision (primary incision) 53 of high self-sealing nature. Such primary incision 53 would have the minimal width to enable insertion of the vacuum nozzle of the phacoemulsification device for vacuuming the crystalline lens.

In a case where an intraocular lens is inserted after a particular portion of the crystalline lens is extracted, the width of the primary incision 53 is typically smaller than the necessary width for inserting the lens since the width of the primary incision 53 is the minimal width for inserting of the vacuum nozzle. Therefore, the width of the primary incision 53 is required to be widened to a width corresponding to the measurement of the intraocular lens. Since there is a risk of damaging the unaffected portion of the crystalline lens with a front tip of the knife 51 when attempting to widen the primary incision using the knife 51 for incising the eyeball, a special knife having a front tip portion without any cutting edge is typically used.

Figure 8:
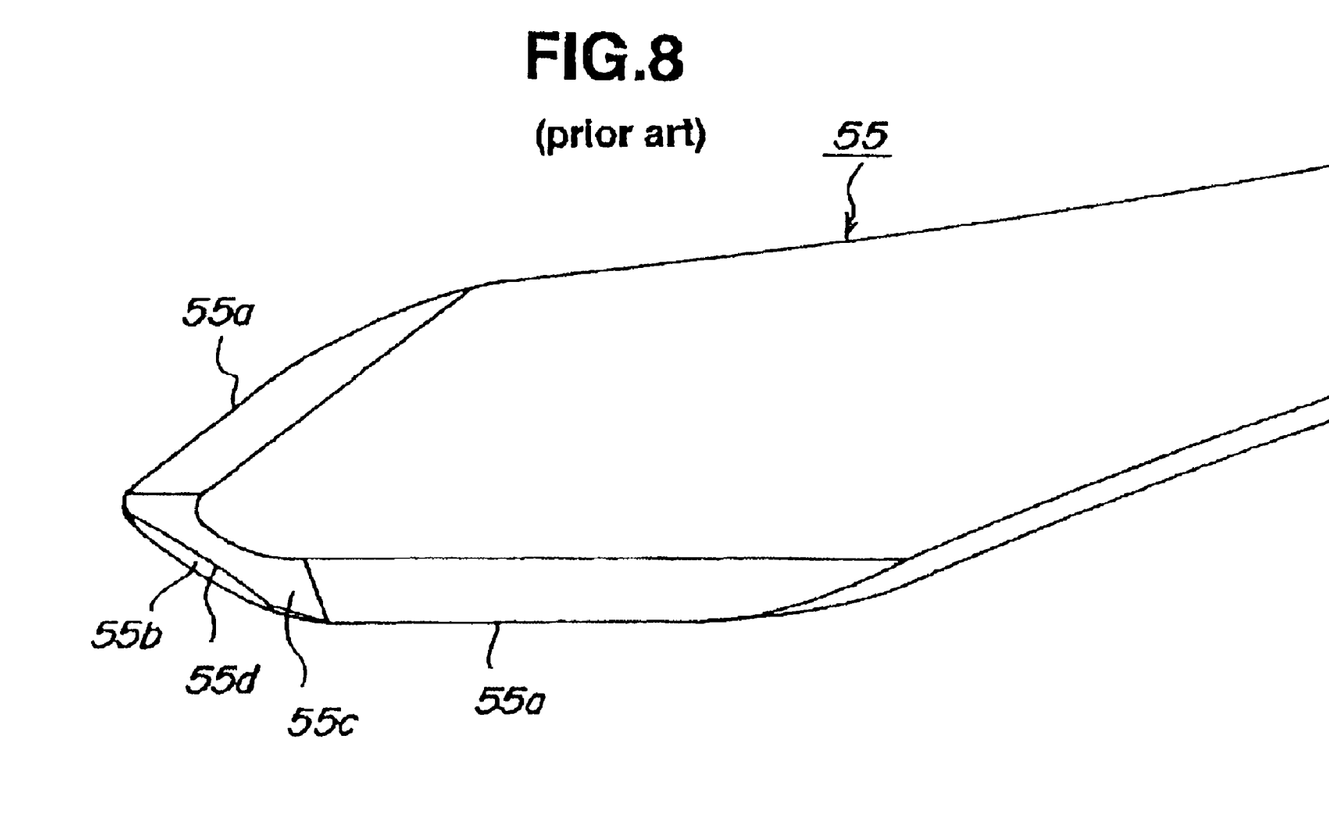
FIG. 8 is a perspective view explaining a structure of a conventional knife for opening a primary incision.
Figure 9:
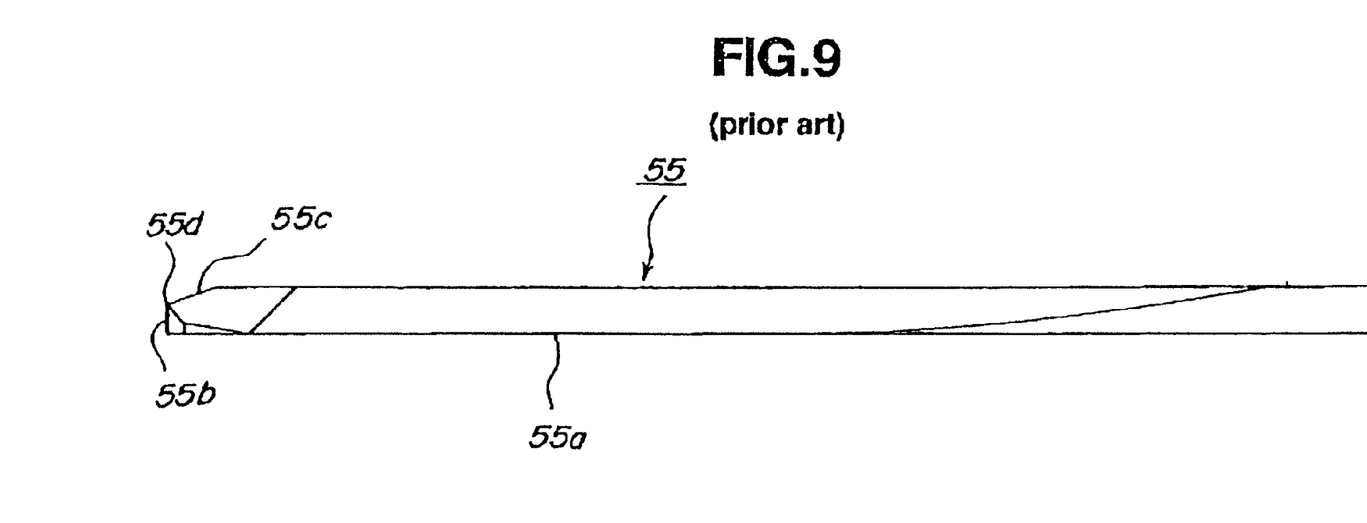
FIG. 9 is an enlarged side view showing an essential portion of the knife in FIG. 8.

An example of a knife used for widening the primary incision 53 will be explained with reference to FIG. 8 and FIG. 9. In the drawing, the knife 55 has a width narrowing toward its front tip portion, and is provided with cutting edges 55*a* formed on both sides. The front tip portion has a flat surface 55*b* formed substantially perpendicular to the axis of the knife 55. A slope 55*c* is formed at a topside of the front tip portion, in which the slope 55*c* is connected with the flat surface 55*b*. Accordingly, a cutting edge capable of incising the eyeball is not formed at the front tip portion of the knife 55, and an obtuse edge 55*d* with an angle no less than 90 degrees is formed in which the obtuse edge 55*d* is formed with the flat surface 55*b* contacting to a rim portion of the cornea 52 comprising the primary incision 53, and the slope 55*c* connecting to the flat surface 55*b*.

Figure 10:
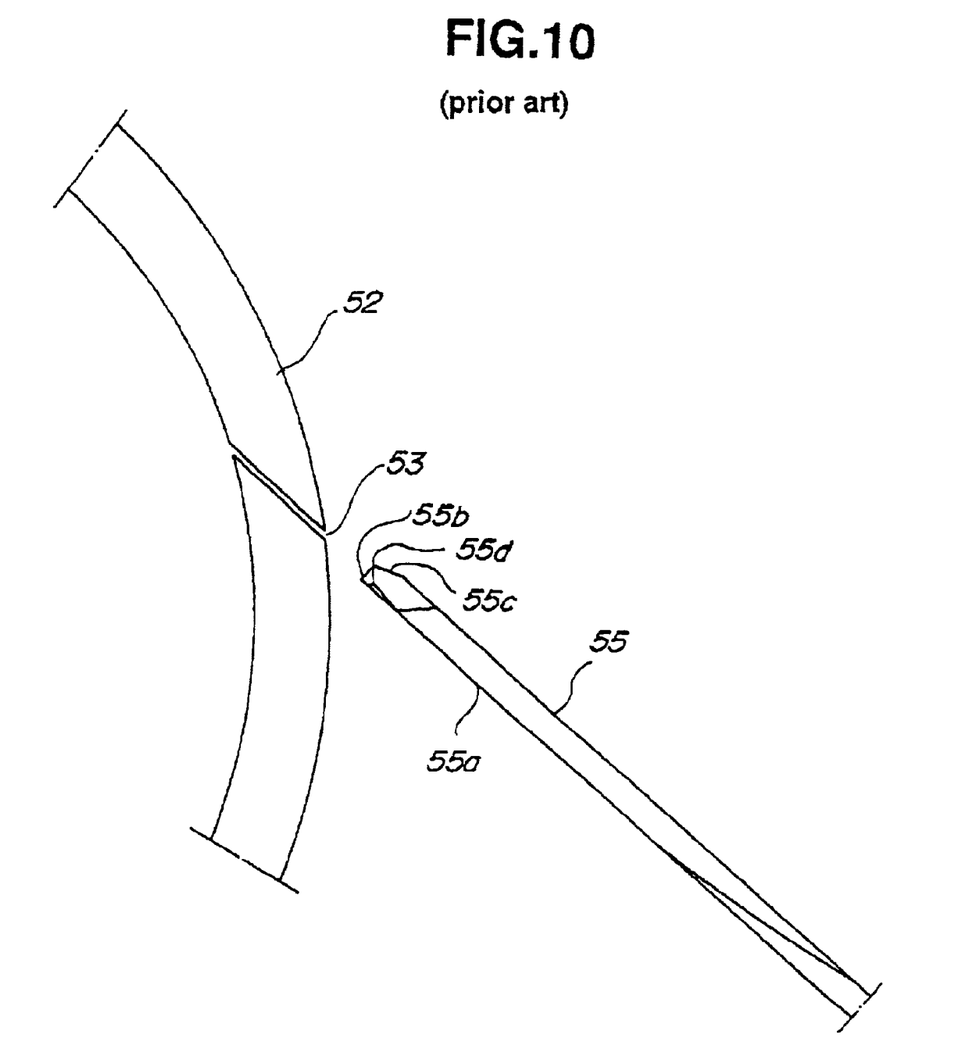
FIG. 10 is a view for explaining a problem regarding the conventional knife.

As shown in FIG. 10, when widening of the primary incision 53 is attempted by inserting the knife with the flat surface 55*b* and the obtuse edge 55*d* into the primary incision 53 formed at the cornea 52, due to the high self-sealing nature of the primary incision 53, the flat surface 55*b* of the knife 55 would contact and be caught to the rim portion of the cornea comprising the primary incision 53 to raise a problem of preventing the knife 55 from being inserted smoothly into the primary incision 53.

Along with such problem, there are risks as scraping the eyeball with the flat surface 55*b* of the knife 55 or damaging the cornea 52 by rolling the cornea 52 upward, and further, increasing the burden of the physician.

When using a knife formed with a cutting edge on a front tip portion to avoid such problems, problems such as the risk of newly incising the surrounding of the primary incision or affecting the self-sealing nature of the primary incision would be created.

It is an object of this invention to provide an ophthalmologic knife capable of being easily guided inside when widening a highly self-sealing incision formed at the eyeball, without a risk of damaging the cornea surrounding the incision or the crystalline lens.

SUMMARY OF THE INVENTION

In means to solve the foregoing problems, the present invention is an ophthalmologic knife for being guided into an incision formed at an eyeball and widening the width of the incision, the ophthalmologic knife comprising: a handle; and a blade portion having a flat shape formed at a tip portion of the handle, wherein the blade portion is formed with cutting edges arranged on both sides in a narrowing manner toward a front tip of the blade portion, and wherein the front tip of the blade portion is formed with a guide portion arranged between the two cutting edges for guiding the blade portion into the incision formed at the eyeball.

With the aforementioned ophthalmologic knife (hereinafter referred as simply "knife"), since the cutting edges are arranged on both sides in a narrowing manner toward a front tip of the blade portion and since a guide portion with a wedge shaped cross section for guiding the blade portion into the incision formed at the eyeball is arranged at the front tip portion of the blade portion between the two cutting edges, the guide portion allows the front tip of the blade portion of the knife to be easily guided to the primary incision without damaging the surface of the eyeball. Accordingly, the blade portion could be guided inside, the width of the primary incision could be widened by the cutting edges formed along the blade portion in a longitudinal direction, and a secondary incision corresponding to the measurement of the intraocular lens could be formed, without damaging the surrounding of the primary incision.

The guide portion is required to be guided with extreme ease into the primary incision formed beforehand at the eyeball. The shape required for such guide portion is a shape capable of being easily guided into the primary incision without incising the eyeball. Accordingly, it is preferable for the angle of the guide portion to be sufficiently greater than that of the cutting edge; further, it is preferable not to have a flat surface, which would make direct contact to the incised rim portion of the cornea when guiding the blade portion into the primary incision. It is preferable for the guide portion to not have a flat surface intersecting perpendicular to an axis of the blade portion; further, it is preferable for the front tip of the guide portion to have at least one slope on either the top or the bottom surface, and the angle for both the top and bottom surface should range between approximately 36 degrees through 150 degrees.

However, the function of the guide portion is to easily and steadily guide the blade portion toward the highly self-sealing primary incision formed at the eyeball, and the angle for the top and bottom surface is not to be limited to the aforementioned range.

It should now be noted that the bordering portion between the cutting edge and the guide portion should preferably become sharper from the guiding portion toward the cutting edge, and in such case, the width of the guide portion should be at least narrower than the width of the primary incision. In respect of the bordering portion, although the angle from the guide portion to the cutting edge could change abruptly, there should be no difference in level, which would damage the eyeball during insertion into the primary incision or when drawing out the blade portion from the primary incision.

BRIEF DESCRIPTION OF THE DRAWINGS

The above and other objects and features of the invention are apparent to those skilled in the art from the following preferred embodiments thereof when considered in conjunction with the accompanied drawings, in which.

DESCRIPTION OF THE PREFERRED EMBODIMENTS

Figure 1:
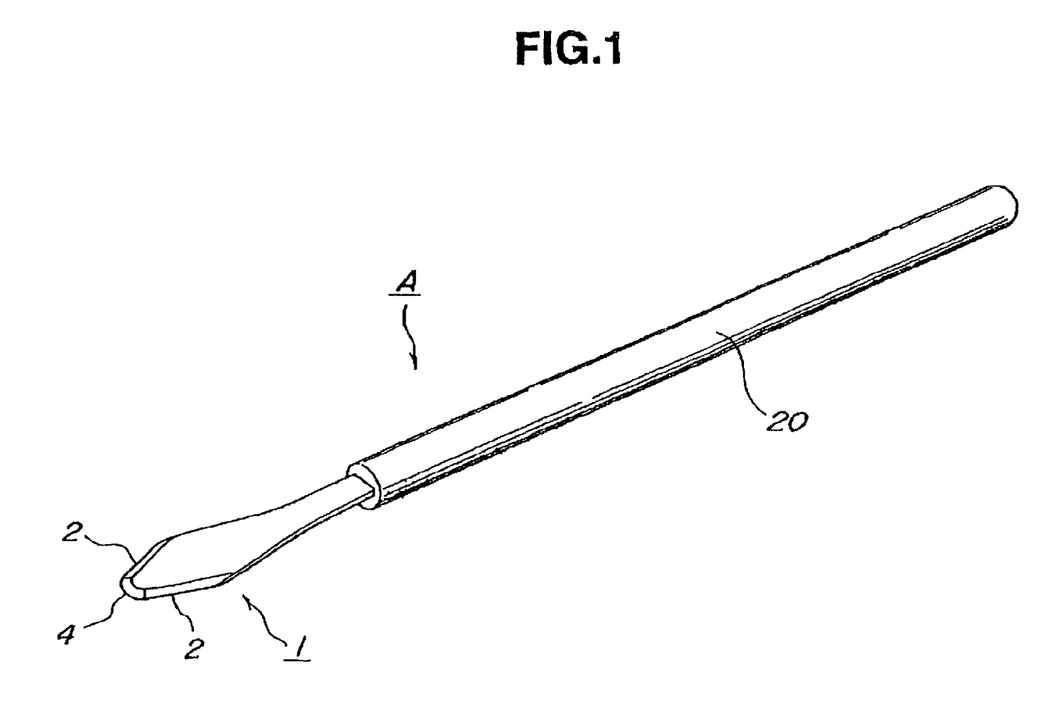
FIG. 1 is a perspective view showing a knife for the first embodiment.
Figure 2:
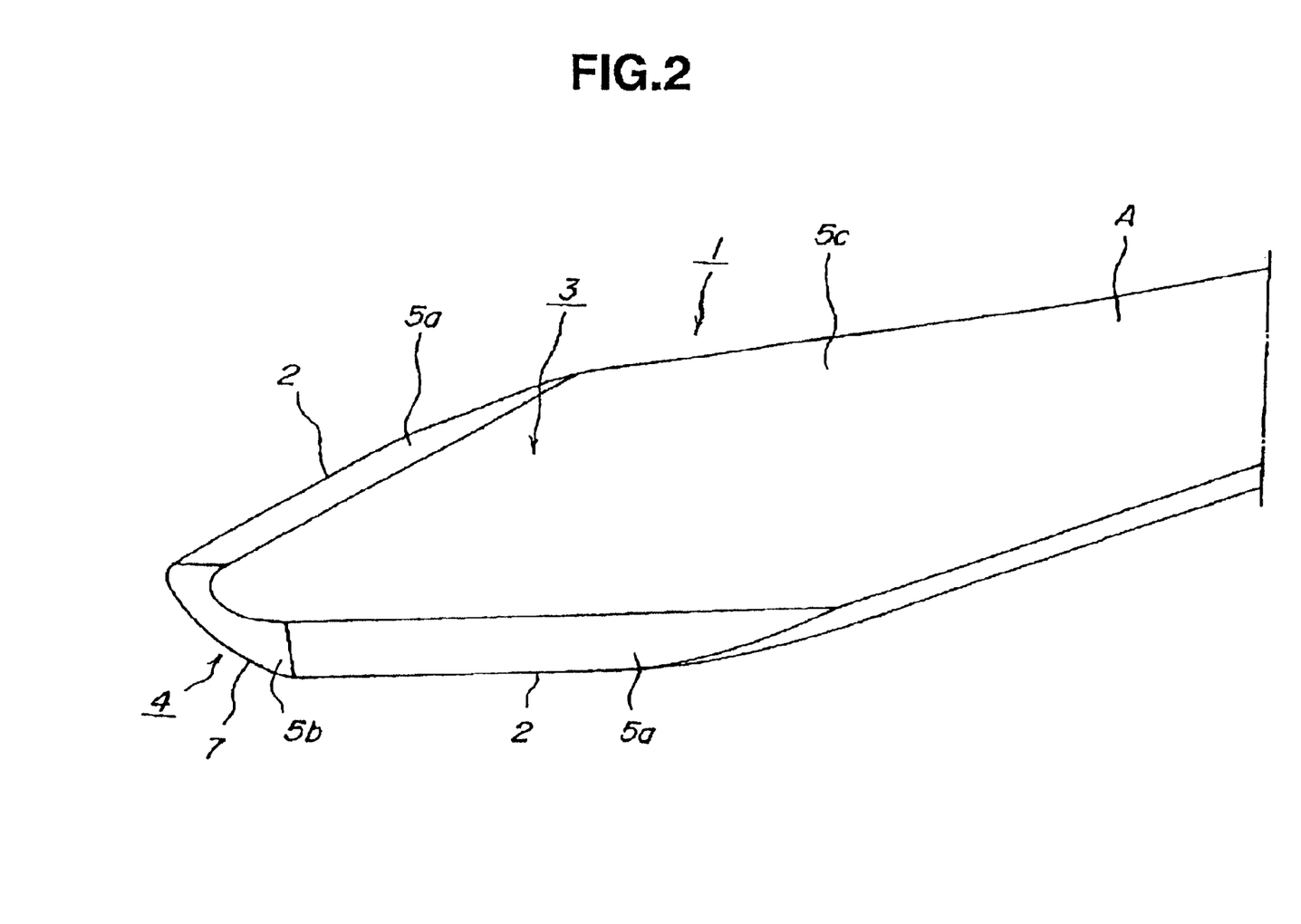
FIG. 2 is a perspective view showing a blade portion of a knife for the first embodiment.
Figure 3:
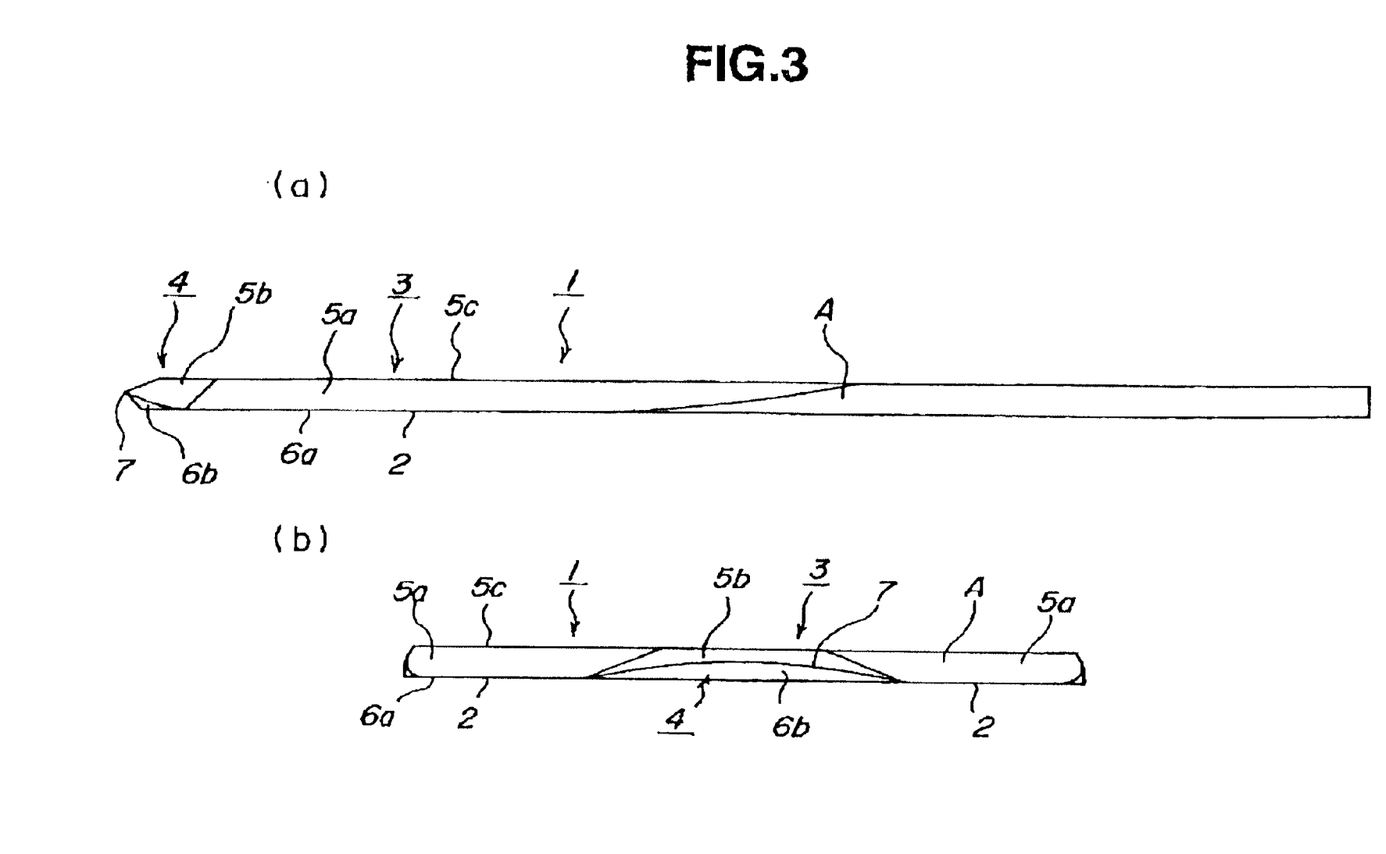
FIG. 3 is a side view and a front view showing a knife for the first embodiment.
Figure 4:
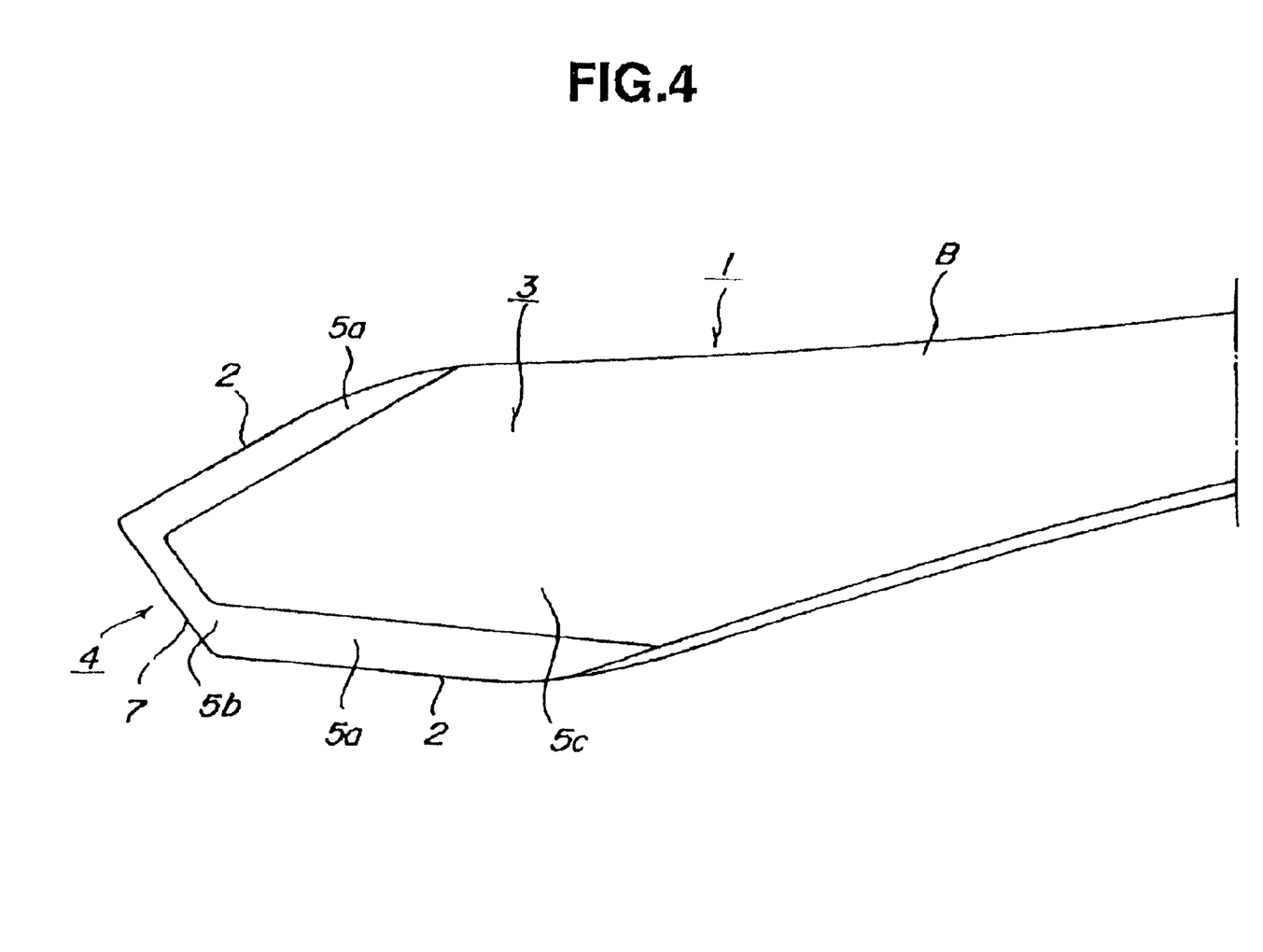
FIG. 4 is a perspective view showing a knife for the second embodiment.
Figure 5:
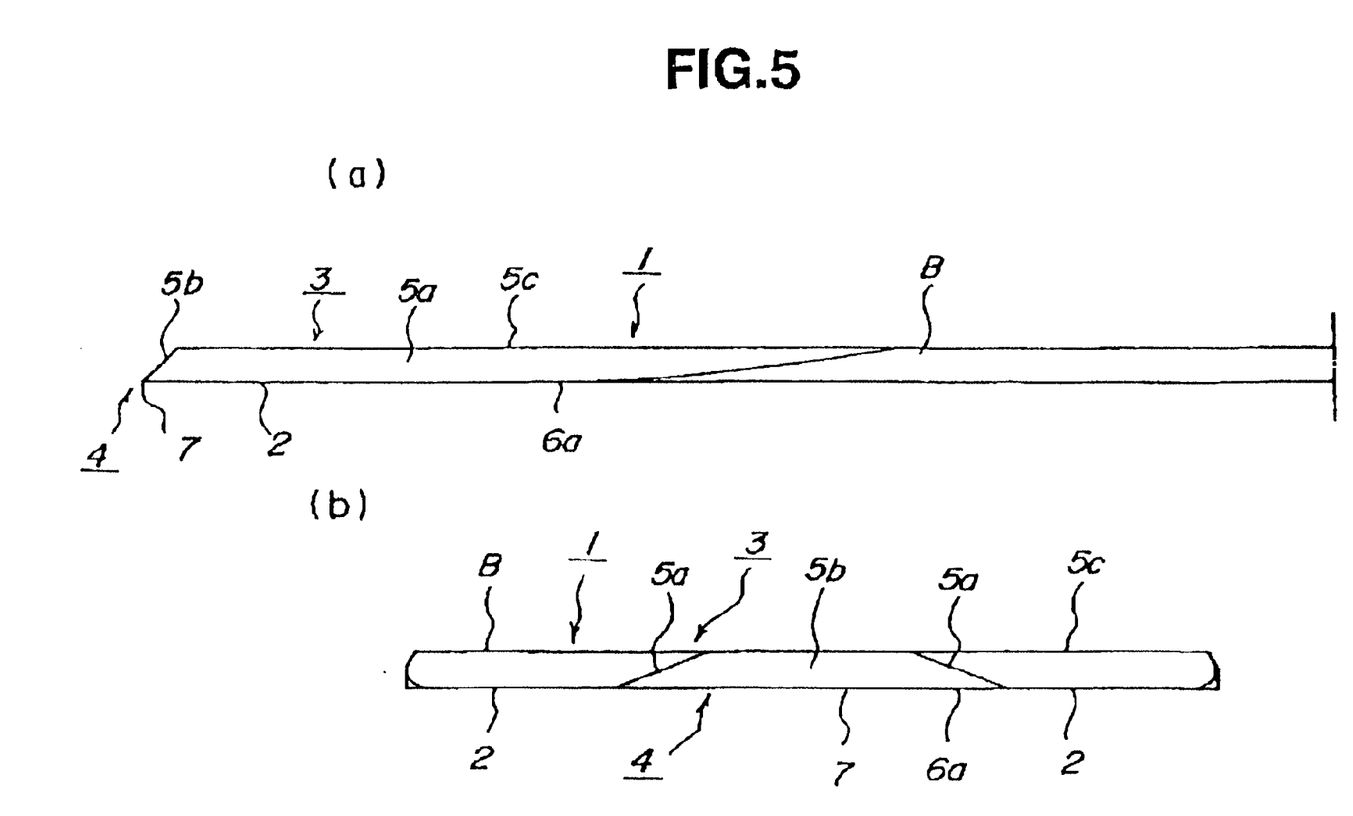
FIG. 5 is a side view and a front view showing a knife for the second embodiment.
Figure 6:
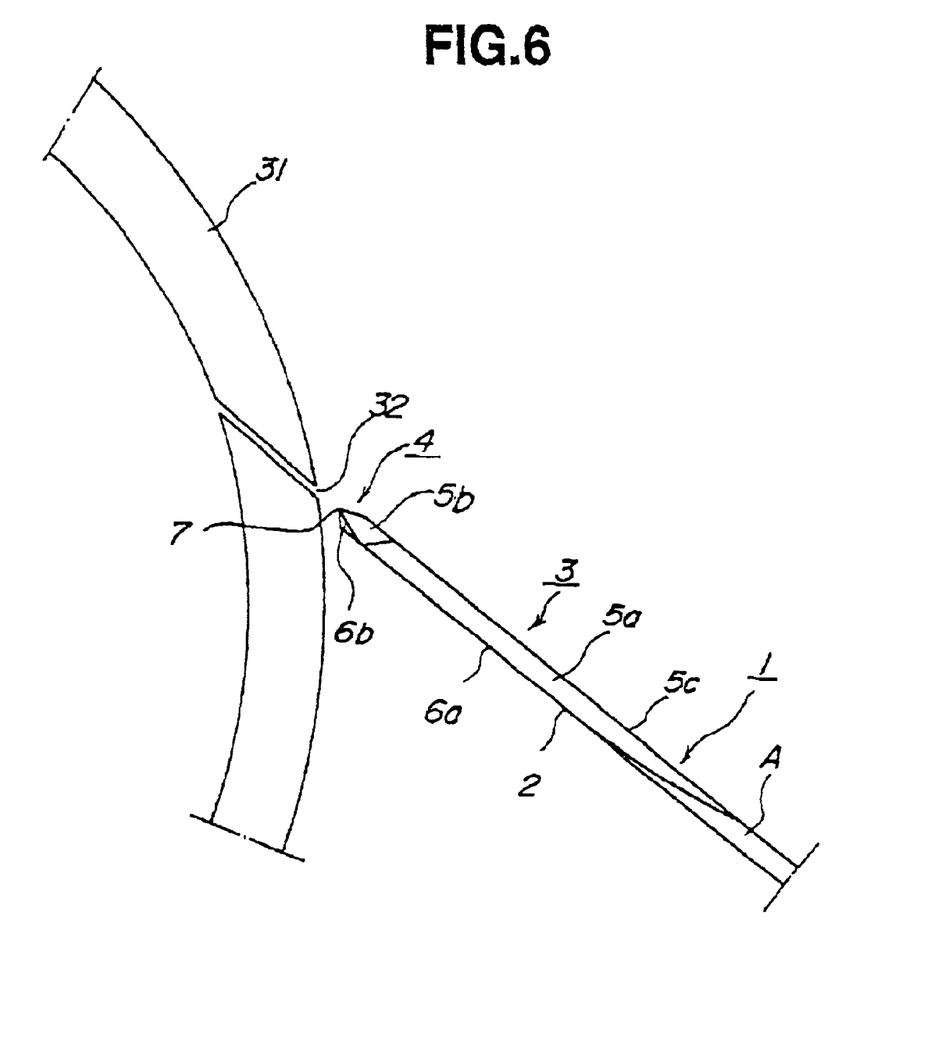
FIG. 6 is an explanatory view showing a relation between an incision and a knife.

A preferred embodiment of the foregoing knife will hereinafter be described with reference to the drawings. FIG. 1 is a perspective view of a knife for the first embodiment. FIG. 2 is an enlarged perspective view of a blade portion of the knife for the first embodiment. FIG. 3 is a side view and a front view of a knife for the first embodiment. FIG. 4 is a perspective view of a knife for the second embodiment. FIG. 5 is a side view and a front view of a knife for the second embodiment. FIG. 6 is a view for explaining a relation between an incision and a knife. Shown in FIG. 1 through FIG. 3 is a knife A for the first embodiment having a structure where a blade portion 1 is attached to one end of a handle 20. As shown in FIG. 6, during surgery of an eyeball, the knife A is aimed to have a blade portion 1 thereof inserted into a highly self-sealing primary incision 32, which is formed at the cornea 31 or the sclera beforehand, and aimed to widen the width of the primary incision 32 into a measurement corresponding to the measurement of an intraocula lens.

The knife A is structured with the blade portion 1 having a predetermined flat shape and a predetermined cross-section, and a shank (not shown) continuing from the blade portion 1, in which the blade portion 1 has a cutting edge 2 formed on both sides, respectively along the blade portion 1 in a longitudinal direction (axial direction continuing from the shank). The shank is fixed to a handle, wherein the handle is held and manipulated by a physician for performing surgery of widening the primary incision 32 formed beforehand at the eyeball, into a width corresponding to the measurement of an intraocular lens.

The maximum width of the cutting edge 2 formed at both sides of the blade portion 1 is predetermined to the size standard of an intraocular lens. Accordingly, the blade portion 1 comprises a main body 3 being substantially of a V letter shape where the measurement becomes narrower from a maximum width portion to a front tip portion, and a guide portion 4 having a gentle curse form, which serves to define the front tip portion of the blade portion 1 and to connect the cutting edges 2 on both sides.

Formed on the top surface of the cutting edge 2 is a top slope 5a, extending from the top slope 5a to the front tip portion is a slope 5b comprising the top surface of the guide portion 4 and having a different inclination angle from that of the Lop slope 5a; and further, a horizontal surface 5c is formed A horizontal surface 6a is formed at the bottom surface of the cutting edge 2, and extending from the horizontal surface 6a to the front tip portion is a slope 6b comprising the bottom surface of the guide portion 4. In other words, the slope 5b and the slope 6b at the bottom forms a wedge-shaped cross section at the side cross section of the guide portion 4 in a longitudinal direction of the ophthalmologic knife A.

Accordingly, the cutting edge 2 is formed with the top slope 5a and the horizontal surface of the bottom side 6a, the front tip portion is formed with an edge 7 comprised of the slope 5b and the slope 6b. More particularly, the cutting edge 2 is formed extending from a portion of the main body 3 having the maximum width to the guide portion 4, and is not formed extending from the maximum width portion to the shank side. A portion extending from the maximum width portion to the shank could be formed in a manner where the maximum width portion is straightly connected to the shank while maintaining maximum width, or as in the embodiment shown in FIG. 1, such portion could be straightly or circularly connected to the shank in a manner where the maximum width portion narrows in a tapered manner.

During surgery of an eyeball, the cutting edge 2 serves to incise the cornea 31 or the sclera for widening the width of the primary incision 32 (a nearer and farther side opposing the surface in FIG. 6) formed beforehand at the cornea 31 and the sclera blade portion 1. Accordingly, the angle of the cutting edge 2 (the angle of the top slope 5a and the horizontal surface of the bottom side 6a) ranges approximately between 10 degrees through 35 degrees, and more preferably, between 12 degrees through 25 degrees.

However, even if the angle of the cutting edge 2 exceeds the foregoing range, the incising of the eyeball does not immediately become impossible; although the difficulty for the physician may increase, the incising could be performed depending on how much is exceeded.

The maximum width of the main body 3, that is, the maximum width of the cutting edge 2 oppositely arranged on both sides of the main body 3 is predetermined in accordance to the type (hard or soft) or measurement of the intraocular lens, and the inserting method thereof. For example, as for the maximum width predetermined in accordance with the intraocular lens, there are size standards such as 3.75 mm, 4.1 mm, and 5.2 mm; as for others, there are size standards as 3.5 mm and 5.5 mm. In any case, the maximum width of the main body 3 is based on the size standard of the intraocular lens, and is not to be limited to the aforementioned measurements.

Although the thickness of the main body 3 is not to be limited, the thickness thereof is required to be a measurement, which would not damage the cornea 31, the sclera or the crystalline lens when inserted into the primary incision 32. Further, by forming the main body 3 into a suitable thickness, the guiding of the blade portion would become easier. Accordingly, the thickness of the main body 3 ranges from 0.14 mm through 0.20 mm However, the thickness is not to be limited to the aforementioned measurement.

The flat shape of the main body 3 regarding this embodiment is comprised of cutting edges 2 extending from the maximum width portion to a front tip portion in a substantially straight manner so as to form a V letter shape with a bottom (the bottom corresponds to the guide portion 4). However, the flat shape of the main body 3 is not to be limited to the aforementioned, and could also be of a gentle curved shape extending from the maximum width portion to the front blade portion with the cutting edges 2 formed at the curved portion.

The guide portion 4 is formed at the flat shape of the main body 3 in a gentle curved manner connecting the cutting edges 2 formed on both sides of the main body 3. By forming the guide portion 4 in a curved manner, a portion of the guide portion 4 contacts upon the primary incision 32 so that guidance could be performed smoothly when inserting the knife A into the primary incision 32. Nevertheless, since the primary incision 32 is formed upon a spherical shaped eyeball, guidance could be performed even with a straight shaped guide portion 4, such as knife B (described afterwards).

Although the width of the guide portion 4 is required to be smaller than the width of the primary incision formed at the eyeball, the flat shape is not required to have a sharp tip. In other words, since the guide portion 4 serves to guide the blade portion 1 to the primary incision 32 without incising the cornea 31 or the sclera, a portion of the guide portion 4 is just required to be smoothly guided into any portion of the primary incision 32. Accordingly, in means to accomplish such performance, the guide portion 4 is required to have a width smaller than the width of the primary incision 32.

In this embodiment, the guide portion 4 is formed with the edge 7 comprising the slope 5b and the slope 6b arranged above and below. The edge 7 is formed on the front tip of the blade portion 1 in a front ward projecting manner, and is smoothly guided into the primary incision 32 between the end portions of the cornea 31 in means to guide the knife A.

In other words, the edge 7 is just required to be guided smoothly into the primary incision 32, and is not to incise the cornea 31 surrounding the primary incision 32 or the crystalline lens.

Therefore, the angle of the edge 7 (the angle comprised by the slope 5b and the slope 6b) is predetermined to range from 36 degrees through 150 degrees, and more preferably to range from 36 degrees through 90 degrees. When the angle of the edge 7 is no more than 30 degrees, the edge 7 would become relatively sharp to cause a risk of incising or damaging the cornea 31 or the crystalline lens when the knife A is guided into the primary incision 32. When the angle of the edge 7 is more than 100 degrees, the edge 7 might be caught to the primary incision 32 at the end portion of he cornea 31 and might prevent the knife A from being guided smoothly inside.

The length from the maximum width portion of the cutting edge 2 to the front tip portion is no less than 3 mm so that insertion into the primary incision 32 could be performed easily.

It should now be noted that when the width of the front tip (the width of the guide portion 4 described afterwards) is no more than 60% of the maximum width (that is, when the blade portion is sharper), it is preferable for the angle of the guide portion 4 to be of an obtuse angle ranging from 80 degrees through 150 degrees so that insertion would be difficult and the damaging of the crystalline lens could be prevented.

More particularly, in means to prevent the edge 7 from incising, the intersecting portion between the slope 5b and the slope 6b (the edge 7) could be formed not of an edge-like shape, but of a curved shape (chamfering). In this case, since the edge 7 hardly has much incisiveness, the angle of the edge 7 could be reduced so that the guiding into the primary incision 32 could be performed more smoothly Regarding the thus structured knife A, as shown in FIG. 6, when the blade portion 1 is faced against the primary incision 32 formed at the eyeball, the edge 7 of the guide portion 4 defining the front tip of the blade portion 1 faces in-between the cornea 7 structuring the primary incision 32. In such state, when the knife A is driven forward, the knife A easily penetrates the primary incision 32 since the edge 7 is shaped in a forward protruding manner, and is guided inside the eyeball by having the slope 5b and the slope 6b comprising the edge 7 to push aside the cornea 31 of the primary incision 32. In such case, the guide portion 4 including the edge 7 would not damage the cornea 31 surrounding the primary incision 32, the sclera, or the crystalline lens.

Along with the advancing of the blade portion 1 into the eyeball, the cutting edge 2 continuing to the guide portion 4 is guided into the primary incision 32, and incises the primary incision 32 for widening both ends of the primary incision 32 in a width direction. When the maximum width portion of the cutting edge 2 for the blade portion 1 has passed the primary incision 32, the primary incision 32 forms a secondary incision having a prescribed width corresponding to the measurement of an intraocular lens or corresponding to a method of inserting such lens.

During the forming of the secondary incision where the cutting edge 2 formed along the blade portion 1 in a longitudinal direction widens the primary incision 32 in the width direction, even though the guide portion 4 enters between the cornea 31 and the crystalline lens, incision could be securely performed without having to damage the crystalline lens or the surrounding of the primary incision 31, since the edge 7 of the guide portion 4 does not have an incisive angle.

The knife A is required to demonstrate a satisfactory cutting quality during surgery, and is required to be rust-resistant during distribution and storage. During production of the knife A, it is preferable to use an austenite stainless steel wire for the material of the knife A; a high rigidity could be obtained from work hardening and the texture could be expanded into a fiber-like form by processing the wire with cold wire-drawing.

When manufacturing the knife A, the aforementioned wire like material is press worked or a plate-like material is press worked so as to form an intermediate product including the blade portion 1 and the shank, and further, the cutting blade 2 and the guide portion 4 could be formed by cutting and grinding the intermediate product.

More particularly, when forming the cutting edge 2 upon the blade portion 1, the cutting edge 2 is commonly formed by grinding or polishing with grindstone or a lapping film. Further, when forming the guide portion 4, it is possible to use the grinding or polishing method in the same manner as forming the cutting edge 2; further, it is possible to simply cut the guide portion 4 to form a prescribed slope during press working. Further, after forming the flat shape of the blade portion 1 into a prescribed shape, the surrounding could be grinded or polished to form the cutting edge 2 and the guide portion 4, and then, the surface could be processed by performing chemical polishing or electrolytic polishing.

It should now be noted that although an austenite stainless steel is used as the material for the knife A in this embodiment, the material is not to be limited; for example, the same result could be obtained even when a quenchable martensite stainless steel is used; and further, materials such as diamond or ruby could also be used. In other words, as long as the characteristic required for an ophthalmologic knife is fulfilled, the material thereof is not to be limited.

Further, since an ophthalmologic surgery is surgery of extreme delicacy, such surgery is performed with a microscope. Accordingly, halation might be caused from the light of the lighting reflected by the surface of the blade portion 1. Such case would cause unnecessary strain for physicians; therefore, it would be preferable to apply a reflection-prevention treatment such as providing minute jaggedness upon the blade portion 1. Since applying a reflection-prevention treatment upon the cutting edge may lower the cutting quality, it is preferable to apply the reflection-prevention treatment only upon the guide portion 4 and the horizontal surface 5c.

Although the knife A is formed in a straight shaped manner extending from the blade portion 1, the shank, and to the handle, it is not necessary for the knife A to be formed in such straight manner, instead, the blade portion 1 could be of a spoon like shape formed with a prescribed angle against the handle.

Further, it is preferable for information such as the size or the maximum width of the knife A to be indicated upon the blade portion 1, the shank, or the handle by means such as engraving.

Next, a second embodiment regarding the structure of knife B will be described with reference to FIG. 4 and FIG. 5. It should be noted that portions or functions similar to those explained in the first embodiment will be assigned with the same reference numerals, while omitting the explanations thereof.

Shown in the drawing is the knife B, in which an edge 7 comprising a guide portion 4 is shaped substantially straight at a front tip of a blade portion 1, and the edge 7 along with the cutting edges 2 would form three lines for forming the blade portion 1 into a trapezoid flat shape.

The guide portion 4 of the knife B is comprised of the edge 7, wherein the edge 7 is structured with a slope 5b extending from a top slope 5a formed on the top surface of the cutting edge 2 and having a different angle from that of the top slope 5a, and a bottom horizontal surface 6a. In other words, at a side cross-section in the longitudinal direction of the ophthalmologic knife B, the guide portion 4 has a wedge shaped cross section comprised of the edge 7 formed with the slope 5b and the horizontal surface 6a. Accordingly, the edge 7 is formed in a manner where one side is a slope, and the other side is a horizontal surface, and formed in a manner matching at the bottom surface of the blade portion 1.

Even with the aforementioned edge 7, the edge 7 is shaped projecting front ward from the front tip of the blade portion 1, which is of a structure no different from that of the edge 7 of the knife A of the first embodiment. Even with the aforementioned edge 7, the range for the angle of the edge 7 is set to the same range as in the first embodiment.

Even with the thus structured knife B, since the eyeball is of a spherical shape, the primary incision 32 formed beforehand is an arc-like shape, and when the edge 7 approaches the primary incision 32, the edge 7 and the primary incision 32 would not entirely make contact with each other, but would make partial contact to each other. Accordingly, the edge 7 could enter and pressingly widen in between the cornea 31 forming the primary incision 32 and could smoothly guide the blade portion 1 inside. Subsequently, the cutting edges 2 could form a secondary incision by incising and widening the primary incision 32 to both sides in a width direction.

Consequently, as described in detail, in respect of the knife regarding this invention, a blade portion could easily be guided into the primary incision by forming cutting blades respectively along a blade portion in a longitudinal direction and by arranging the guide portion 4 at the front tip of the blade portion for guiding the blade portion to the primary incision formed at the eyeball beforehand. Accordingly, the blade portion could be guided inside, the cutting edges formed in a longitudinal direction of the blade portion could widen the width of the primary incision, and a secondary incision corresponding to the measurement of an intraocular lens could be formed.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. An ophthalmologic knife for being guided into an incision formed at an eyeball and for widening the width of the incision, said knife comprising:

a handle having an end portion; and a blade portion having a flat shape formed at the end portion of said handle, said blade portion having:

a front tip, two cutting edges arranged on both sides of said blade portion in a narrowing manner toward the front tip of the blade portion, and a guide portion disposed in a width direction of the blade portion having an arc-shaped edge without a sharp tip disposed between the two cutting edges for guiding the blade portion into the incision formed at the eyeball, having a bottom surface, a top surface, a wedge-shaped cross section formed at a side cross section thereof in a longitudinal direction of the knife, cross sectional slopes formed at both the top surface and bottom surface thereof, and having a greater angle than that of the cutting edges, the top surface having an inclination angle different from that of the bottom surface.

2. The ophthalmologic knife according to claim 1, wherein the bottom surface of the guide portion has an inclination angle greater than that of the top surface.

3. The ophthalmologic knife according to claim 1, wherein a flat surface of the guide portion is comprised of a straight portion and an arc portion continuing to the cutting edges on both sides.

4. The ophthalmologic knife according to claim 1, wherein the guide portion is treated with reflection prevention upon the surface thereof.

5. The ophthalmologic knife according to claim 1, wherein the arc-shaped linear edge of said guide portion has an angle of from 36 to 150 degrees.

6. The ophthalmologic knife according to claim 1, wherein the arc-shaped linear edge of said guide portion has an angle of from 36 to 90 degrees.

7. The ophthalmologic knife according to claim 1, wherein the guide portion has a width of 60% or less that of a maximum width of the knife.

* * * * *